United States Patent [19]

Ulrich

[11] 4,292,964

[45] Oct. 6, 1981

[54] METHOD OF AND APPARATUS FOR PINNING A FRACTURED PELVIS

[76] Inventor: Max B. Ulrich, Amselweg 55, 7900 Ulm, Fed. Rep. of Germany

[21] Appl. No.: 112,821

[22] Filed: Jan. 17, 1980

[30] Foreign Application Priority Data

Jan. 19, 1979 [DE] Fed. Rep. of Germany ....... 2901962

[51] Int. Cl.³ ............................................... A61F 5/04
[52] U.S. Cl. .............................. 128/92 EB; 128/92 B
[58] Field of Search ........... 128/92 R, 92 EA, 92 EB, 128/92 B, 92 A, 83

[56] References Cited

U.S. PATENT DOCUMENTS

| 3,704,702 | 12/1972 | Halloran | 128/92 EB |
| 3,892,232 | 7/1975 | Neufeld | 128/92 EB |
| 4,159,716 | 7/1979 | Borchers | 128/92 EA |

FOREIGN PATENT DOCUMENTS

| 1056372 | 3/1952 | France | 128/92 EB |
| 1448111 | 9/1976 | United Kingdom | 128/92 EB |

*Primary Examiner*—Stephen C. Pellegrino
*Attorney, Agent, or Firm*—Karl F. Ross

[57] ABSTRACT

A fractured pelvis is pinned using a guide apparatus comprising an elongated member provided with a pair of longitudinally spaced and transversely projecting arms having outer ends provided with respective coaxially aligned cannulas having points directed at each other and separated by a space. The fractured bone is positioned in the space between the cannulas with the points engaging the fractured bone and holes are formed in the bone surface using trocars through the cannulas. Then a relatively small-diameter guide rod is inserted axially through the cannulas and through the fractured bone engaged therebetween. The guide apparatus is then disengaged from the bone, but the small-diameter guide rod is left in place therein. A tubular drill bit is then fitted over one end of the guide rod and a bore is drilled through the bone along the guide rod while the bit is guided through the bone along this rod. The guide rod is then withdrawn from the bit which itself is left in the bore through the fractured bone. Then the bit is pushed axially out of the bore it has formed by the bone pin whose ends are axially oppositely braced against the opposite ends of the fractured bone.

10 Claims, 9 Drawing Figures

FIG.1A
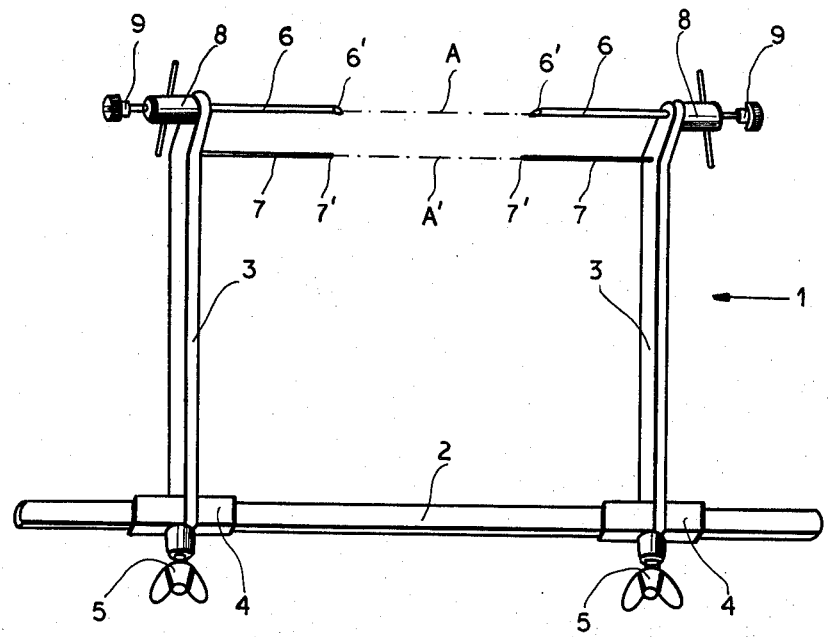
FIG.1B
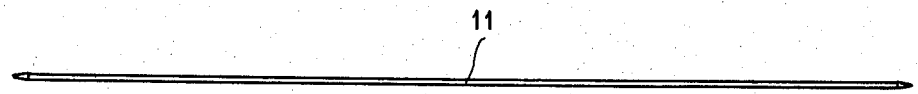
FIG.1C
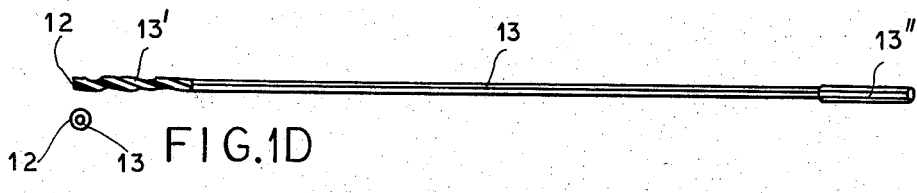
FIG.1D
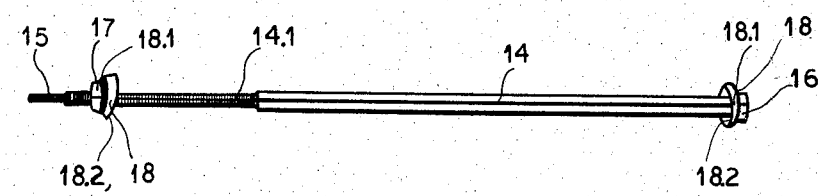
FIG.1E 4,292,964

METHOD OF AND APPARATUS FOR PINNING A FRACTURED PELVIS

FIELD OF THE INVENTION

The present invention relates to a method of and apparatus for pinning a bone. More particularly this invention concerns a method and apparatus particularly usable with a fractured pelvis.

BACKGROUND OF THE INVENTION

When a pelvis is broken at the joint, particularly when the symphysis is broken and/or the sacro-iliac articulation is damaged, it is normally considered impossible to pin the fractured bone. As the spinal column is dangerously close to the region where the pin would have to run, it is considered too risky to attempt to implant a pin into the fractured bone. Hence, the fracture is normally merely reduced, then the patient is placed in a body cast and must remain immobile for several months while the bones knit. Obviously such a procedure is extremely time-consuming, costly, and wasteful of valuable health resources,

OBJECTS OF THE INVENTION

It is, therefore, an object of the present invention to provide an improved method of and apparatus for pinning a bone.

Another object is to provide such a method and apparatus which allow a pin to be implanted through the sacro-iliac bones without endangering the spinal column or nerves emanating therefrom.

SUMMARY OF THE INVENTION

These objects are attained according to the instant invention in a bone-pinning method which employs a guide apparatus comprising an elongated member provided with a pair of longitudinally spaced and transversely projecting arms having outer ends provided with respective coaxially aligned cannulas having points directed at each other and separated by a space. According to this invention a fractured bone is positioned in the space between the cannulas with the points engaging the fractured bone. An X-ray can ascertain that the axis defined between these points lies wholly in the bone, and avoids any delicate soft tissue. Then, according to this invention, a relatively small-diameter guide rod is inserted axially through the cannulas and pierces through the fractured bone engaged between these cannulas. The apparatus is then disengaged from the bone, but the small-diameter guide rod is left in place in the bone. A tubular drill bit is then fitted over the guide rod that is engaged in the bone and it drills through the bone along the guide rod with the bit being guided on this rod through the bone. The guide rod is then withdrawn from the bit which itself is left in the bore in the fractured bone. Thereupon the bit is axially retracted from the bore while simultaneously and synchronously a bone pin is inserted axially through the bore. Finally the ends of the bone pin are braced axially oppositely on the fractured bone. In this manner the reduced fractured bone can be pinned in a multi-step procedure that ensures that at no time can the starting guide rod, the drill bit or the bone pin deviate from the selected axial path. It is therefore possible to place the pin in locations where it would normally be considered impossible to operate, as even a small deviation of the drill bit from the decided path could result in a serious nerve damage.

According to further features of this invention each of the arms on the guide apparatus is provided between the respective cannula and the guide member with a positioning rod extending parallel to the respective cannula and having a tip approximately level with that of the respective cannula. These positioning or support rods are engaged against the bones to be joined to maintain the proper position for the guide apparatus while the cannulas, which according to this invention can be provided with respective trocars, are driven through surrounding tissue to the outer surfaces of the fractured bone prior to passing of the guide rod through them.

According to this invention the bone pin has a tip of a diameter approximately equal to that of the guide rod. Thus once the bit is drilled through the bone the tip of the bone pin is fitted into the end of the drill, and the pin itself is used to push the drill out of the bore, simultaneously axially inserting the bone pin in the bore formed by the bit, so that at no time is the reduced fracture able to shift.

As normally the surfaces of the bone being bored lie at the mouths of the bore at an angle to the axis of the bore, according to this invention wedge-shaped washers are provided at the ends of the bolt. The bolt can, therefore, bear with equal axial force all around the bore on the bone surface surrounding the bore. As a result of this good surface contact extremely firm pinning of the fractured bone is ensured.

According to further features of this invention the cannulas are longitudinally displaceable on the respective arms. With such an arrangement the positioning or guide apparatus can first be mounted on the bone to be pinned by means of the above-mentioned holding pins or points. Then the cannulas are screwed into the outer arm ends until they contact the bone surfaces along the required axes. Trocars are provided in these cannulas, having solid points which can be drilled through the surrounding skin and tissue directly to the bone surfaces. Then the trocars are withdrawn so that the above-described guide rod can be inserted.

With the system according to the instant invention it is therefore possible to pin a sacro-iliac fracture of a pelvis without endangering the lumbar portion of the spinal column. Such pinning of even relatively complex pelvic fractures allows the hospital stay for the patient to be reduced to about six weeks from several months, thereby economizing scarce health care facilities, while allowing the patient to recuperate at home under more comfortable circumstances.

BRIEF DESCRIPTION OF THE DRAWINGS

FIG. 1A is a perspective view of the guide apparatus according to this invention;

FIGS. 1B and 1C are side views of the guide rod and drill bit respectively, usable with the apparatus in FIG. 1;

FIG. 1D is a cross section through the bit of FIG. 1C;

FIG. 1E is a side view of the bone pin used with the apparatus according to this invention;

SPECIFIC DESCRIPTION

Figure 2:
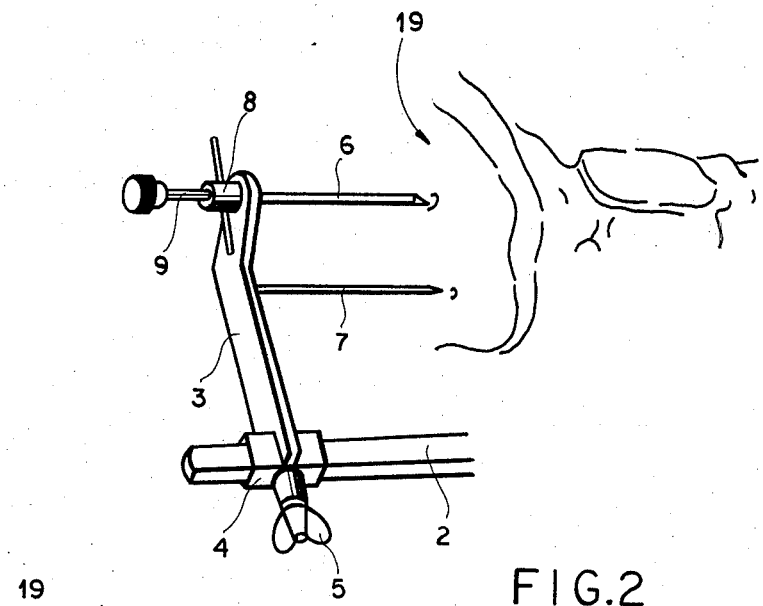
FIG. 2 is a perspective view showing the guide apparatus according to the instant invention in use.

As seen in FIG. 1A the guiding or aiming device 1 according to this invention basically comprises a rigid longitudinally extending guide rail 2 of square section and having a pair of transversely extending arms 3 that can slide longitudinally on the rail by means of feet 4 that in turn can be secured by means of wing screws 5. Each of these arms 3 has an outer end provided with cannulas 6. The two cannulas 6 lie on a common axis A and have points 6' turned toward each other. Insert from each of the cannulas 6 is a positioning pin 7, with the two positioning pins 7 similarly lying on an axis A' parallel to the axis A, and having points 7' turned toward each other. Each of the points 6' is substantially level with the corresponding points 7'. These cannulas 6 are axially displaceable and fixable in nuts 8 on the respective arms 3, and a trocar 9 may be provided for each of the cannulas 6.

FIG. 1B shows a rigid steel guide rod 11 of an outer diameter that is approximately equal to that of the trocars 9, so that the rod 11 can be fitted through the axially aligned cannulas 6.

A drill bit 13 having a central axially throughgoing passage 12 is seen in FIGS. 1C and 1D. This bit 13 has a twist-bit front end 13' of the standard bone-drill type, and a rear end 13" suitable for chucking in a surgical drill.

Finally, FIG. 1E shows a bone pin 14 of an outer diameter substantially equal to that of the drill bit 13, and having at one end a threaded portion 14.1 from the end of which extends a small-diameter portion 15 of the same outer diameter as the guide rod 11. The rear end of bone pin 14 has a head 16 and a nut 17 can be screwed on the threaded portion 14.1. Washers 18 are fittable over the pin 14 immediately adjacent the head 16 and the nut 17, with one face 18.1 of each washer 18 having in a plane perpendicular to the pin 14 and another face 18.2 lying at an angle thereto. Normally a stock of such rods 14 along with a stock of washers 18 having different angles between their inner and outer faces 18.1 and 18.2 are kept on hand by the surgeon.

As shown in FIG. 2 the guide apparatus 1 is fitted to a fractured pelvis bone 19. First of all the two arms 3 are moved into position to that the tips 7' of the positioning rod 7 are seated in the flesh or bone adjacent the location to be pinned. It is then possible to verify by means of an X-ray that the axis A of the cannulas is aligned only with bony material in the desired position, and will not pass through any nerves or the like.

The nut 8 is then rotated so that the cannulas 6 will come to lie tightly against the surface of the bone 19 to be pinned. Then the trocars 9 are driven or screwed in to form small holes in the hard, bony surface.

Figure 3:
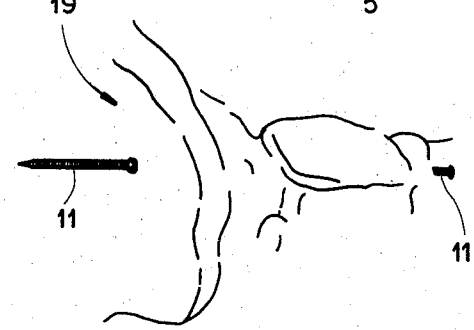
FIG. 3 is a perspective view showing the guide rod in place in a fractured bone.
Figure 4:
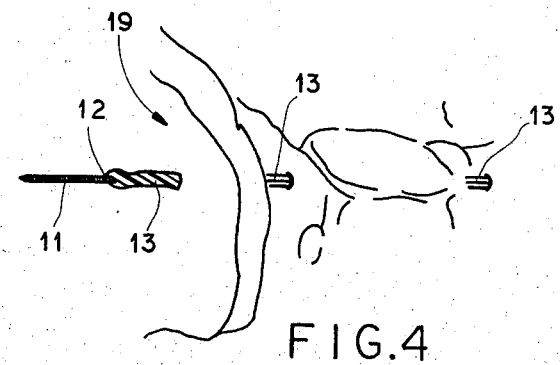
FIG. 4 is a perspective view illustrating the drill bit after it has passed through the fractured bone.

Thereafter the trocars 9 are removed and the double-pointed rod 11 is passed through the bone between the two cannulas 6. The coaxial positioning of these two elements will ensure that the guide rod 11 will follow the exact desired path. Thereupon, as seen in FIG. 3, the cannulas 6 are withdrawn and the apparatus 1 is removed from the site.

The bone drill 13, shown in FIG. 1C, is then fitted with its bore 12 over the rod 11 and is rotated at high speed as it is driven through the bone 19, traversing the fracture. Once the drill 13 is completely through the fractured bone, the guide rod 11 is removed from its passage 12.

Figure 5:
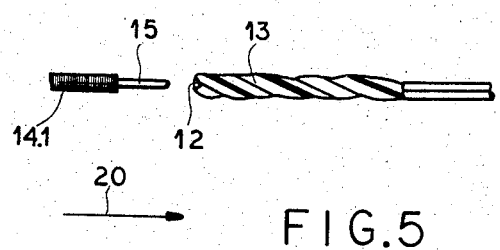
FIG. 5 is a side view illustrating how the drill bit and bone pin according to this invention fit together.

FIG. 5 shows how the tip 15 of the pin 14 is inserted into the hole 12 at the end of the drill 13. The entire pin 14 is then pushed axially in the direction of arrow 20 of FIG. 5 to drive the drill bit 13 axially out of the bore it has formed in the bone 19, thereby replacing it. When it has passed all the way through, the drill 13 is removed from the tip 15. A washer 18 and the nut 17 are then fitted over the threaded end 14.1 and are screwed tight, thereby firmly pinning the fractured bone 19 together.

With the system according to the instant invention it is therefore possible to pin a bone even in a relatively tight position, as adajacent the spinal column. The path along which the bone is to be pinned can be verified, and a preliminary small-diameter hole is formed by the rod 11 which is left in place. The heavier duty drill 13 will then follow the exact path established by this rod 11, and in turn is replaced by the pin 14. Even though considerable force must be brought to bear on the drill bit 13, the pre-positioned guide rod 11 ensures that this drill bit will follow the exact path, as desired, and cannot axially deviate from it. Similarly the pushing of the drill bit 13 out of the hole with the pin 14 prevents any relative displacement of the bone during this delicate operation. Hence, the only operation that is carried out on the reduced fracture before there is anything extending through it to move it from the proper set condition is the insertion of the relatively thin control rod 11. This can be done with relatively limited force so as to prevent destabilizing of the fracture.

It is, of course, possible to use the apparatus method according to the instant invention on fractures other than those of the pelvis. All such obvious variations are well within the purview of the skill of the art.

I claim:

1. A method of pinning a bone using a guide apparatus comprising an elongated member provided with a pair of longitudinally spaced and transversely projecting arms having outer ends provided with respective coaxially aligned cannulas having points directed at each other and separated by a space, said method comprising the steps of sequentially;

positioning a fractured bone in said space between said cannulas with said points engaging said fractured bone; inserting a relatively small-diameter guide rod axially through said cannulas and through the fractured bone engaged therebetween;

disengaging said apparatus from said bone while leaving said small-diameter guide rod in place in said bone;

fitting a tubular drill bit over said guide rod engaged in said bone and drilling a bore through said bone along said guide rod while guiding said bit through said bone along said guide rod;

withdrawing said guide rod from said bit while leaving same engaged through said bore in said fractured bone;

axially retracting said bit from said bone while simultaneously and synchronously axially inserting a bone pin through said bore; and bracing the ends of said bone pin axially oppositely on said fractured bone.

2. The method defined in claim 1 wherein said apparatus includes on each of said arms a positioning rod extending generally parallel to the respective cannula, said positioning rods being substantially aligned and coaxial, said method further comprising the step prior to inserting said guide rod and engaging said points with said bone of positioning said apparatus on said fractured bone by means of said positioning rods.

3. The method defined in claim 1 wherein one end of said pin has a head, said ends of said pin being axially braced by bearing on said bone at said end opposite said head with a nut threaded on said pin.

4. An assembly for pinning a bone, said apparatus comprising:
- an elongated member provided with a pair of longitudinally spaced and transversely projecting arms having outer ends, at least one of said arms being longitudinally relatively displaceable and lockable on said member;
- respective coaxially aligned pointed cannulas mounted on said outer ends with their points directed at each other and separated by a space, whereby a fracture bone to be pinned can be engaged between said points;
- a guide rod engageable axially through said cannulas and through a bone engaged therebetween;
- a tubular drill bit having a central throughgoing passage through which said guide rod is axially engageable as said drill bit bores through a bone through which said rod is engaged;
- a threaded bone pin of an outside diameter equal at most to that of said bit and having a pair of ends normally extending from said bone when said bone pin is engaged through the bore formed by said bit along said guide rod; and
- means for bracing said ends of said pin against said bone.

5. The assembly defined in claim 4 wherein said arms each carry a respective positioning rod extending toward and coaxial with the positioning rod of the other arm.

6. The assembly defined in claim 5 wherein said positioning rods are between said member and the respective cannulas.

7. The assembly defined in claim 4 wherein both said arms are longitudinally relatively displaceable and lockable on said member.

8. The assembly defined in claim 4, further comprising respective trocars engageable through said cannulas to the points thereof.

9. The assembly defined in claim 4 wherein at least one of said cannulas is displaceable toward and away from the other cannula on the respective arm.

10. The assembly defined in claim 4 wherein said means for bracing include wedge-shaped washers engageable between said ends of said pin and said bone.

* * * * *